United States Patent
Truschel et al.

(10) Patent No.: US 9,592,356 B2
(45) Date of Patent: Mar. 14, 2017

(54) SYSTEM AND METHOD FOR IDENTIFYING BREATHING TRANSITIONS

(75) Inventors: William A. Truschel, Eindhoven (NL); Anandi Mahadevan, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 557 days.

(21) Appl. No.: 13/820,856

(22) PCT Filed: Sep. 2, 2011

(86) PCT No.: PCT/IB2011/053849
§ 371 (c)(1),
(2), (4) Date: Mar. 5, 2013

(87) PCT Pub. No.: WO2012/032445
PCT Pub. Date: Mar. 15, 2012

(65) Prior Publication Data
US 2013/0269697 A1 Oct. 17, 2013

Related U.S. Application Data

(60) Provisional application No. 61/381,553, filed on Sep. 10, 2010.

(51) Int. Cl.
*A61M 16/00* (2006.01)
*A61B 5/00* (2006.01)
(Continued)

(52) U.S. Cl.
CPC .... *A61M 16/0057* (2013.01); *A61M 16/0051* (2013.01); *A61M 16/04* (2013.01);
(Continued)

(58) Field of Classification Search
CPC ............ A61M 16/0057; A61M 16/161; A61M 16/0875; A61M 16/04; A61M 16/0666;
(Continued)

(56) References Cited

U.S. PATENT DOCUMENTS 5,469,144 A * 11/1995 Gradzki et al. ............... 340/603
5,503,146 A * 4/1996 Froehlich et al. ....... 128/204.23
(Continued)

FOREIGN PATENT DOCUMENTS

DE 102004014538 A1 10/2005
EP 0722747 A2 7/1996
(Continued)

OTHER PUBLICATIONS

Korten J B et al: "Respiratory Waveform Pattern Recognition Using Digital Techniques", Computers in Biology and Medicine, York, NY, US, vol. 19, No. 4, Jan. 1, 1989, pp. 207-217, XP022875305.

*Primary Examiner* — Bradley Philips
*Assistant Examiner* — Victoria Leszczak
(74) *Attorney, Agent, or Firm* — Michael W. Haas

(57) ABSTRACT

A pressurized flow of breathable gas is delivered to the airway of a subject in accordance with a therapy regimen. One or more fluid parameters of the pressurized flow of breathable gas are adjusted based on the therapy regimen. The therapy regimen dictates that such adjustments be made based on the respiratory state of the subject. Transitions in respiratory state are identified without relying on measurement or estimation of flow at or near the airway of subject. Transitions in respiratory state are identified based on changes in the first time derivative of flow at or near the airway of the subject. In one embodiment, an effort parameter is determined that approximates the second time derivative of flow. Based on comparisons of the effort parameter to a dynamic threshold, transitions in respiratory state are identified.

20 Claims, 4 Drawing Sheets

(51) Int. Cl.
  *A61M 16/04* (2006.01)
  *A61M 16/06* (2006.01)
  *A61M 16/08* (2006.01)
  *A61M 16/16* (2006.01)
  *A61M 16/10* (2006.01)

(52) U.S. Cl.
  CPC .... *A61M 16/0666* (2013.01); *A61M 16/0875* (2013.01); *A61M 16/161* (2014.02); *A61M 2016/0021* (2013.01); *A61M 2016/0027* (2013.01); *A61M 2016/0036* (2013.01); *A61M 2016/102* (2013.01); *A61M 2205/332* (2013.01); *A61M 2205/3365* (2013.01); *A61M 2205/3368* (2013.01); *A61M 2205/3375* (2013.01); *A61M 2205/3569* (2013.01); *A61M 2205/3584* (2013.01); *A61M 2205/3592* (2013.01); *A61M 2205/505* (2013.01); *A61M 2205/52* (2013.01)

(58) Field of Classification Search
  CPC ...... A61M 16/0051; A61 2205/3584; A61M 2205/332; A61M 2205/505; A61M 2205/3375; A61M 2205/3592; A61M 2016/0036; A61M 2205/3569; A61M 2016/102; A61M 2016/0021; A61B 5/00
  USPC .................. 128/204.23, 204.26, 204.22
  See application file for complete search history.

(56) References Cited

U.S. PATENT DOCUMENTS

| | | | |
|---|---|---|---|
| 6,105,575 | A | 8/2000 | Estes |
| 6,237,593 | B1 | 5/2001 | Brydon |
| 6,318,365 | B1 | 11/2001 | Vogele |
| 2002/0185131 | A1 | 12/2002 | Madaus |
| 2007/0084466 | A1* | 4/2007 | Reinstadtler ........... A61B 5/087 128/204.26 |
| 2011/0303223 | A1* | 12/2011 | Kane .................... A61M 16/00 128/204.23 |

FOREIGN PATENT DOCUMENTS

WO  WO 2009149351 A1 * 12/2009
WO  WO2010021556 A1    2/2010

* cited by examiner

SYSTEM AND METHOD FOR IDENTIFYING BREATHING TRANSITIONS

CROSS-REFERENCE TO RELATED APPLICATIONS

This patent application claims the priority benefit under 35 U.S.C. §371 of international patent application no. PCT/IB2011/053849, filed Sep. 2, 2011, which claims the priority benefit under 35 U.S.C. §119(e) of U.S. Provisional Application No. 61/381,553 filed on Sep. 10, 2010, the contents of which are herein incorporated by reference.

BACKGROUND OF THE INVENTION

1. Field of the Invention

The invention relates to the problem of respiratory state transition identification (e.g., accurate and/or systematic detection of the beginning or conclusion of a subjects inspiration or expiration). Proper and synchronous identification of respiratory state transitions are used to adjust or initiate a pressurized flow of breathable gas delivered to the airway of a subject in accordance with a therapy regimen.

2. Description of the Related Art

Systems that deliver pressurized flow of breathable gas to the airway of subjects are known. In conventional systems, one or more fluid parameters of the pressurized flow of breathable gas may be adjusted based on the respiratory state of the subject. For example, it is well known that in machines, such as BiPAP® pressure support system, pressure may be increased during inspiration and reduced during expiration. Typically, transitions in breathing (e.g., from inspiration to expiration and/or from expiration to inspiration) are determined from measurements or estimates of flow in a conduit connected to the patient airway.

Conventional mechanisms for measuring and/or estimating flow at or near the airway of a subject may be costly (in terms of hardware requirements), imprecise, inaccurate and complicate the interface between the patient and the pressure generator. As such, identifications of breathing transitions in the respiration of a subject are compromised by these drawbacks associated with the direct flow measurement proximal to the patient. Consequently, methods of fluid parameter measurement may be done within or near the respiratory device and estimates of the fluid parameters at the patient are performed. In these estimations, the fluid properties are adjusted for parameters such as leak flow or compensated for losses such as pressure loss or heat exchange within the patient circuit. These methods of estimations and compensations are burdened with assumptions regarding the physical characteristics of the patient circuit and require an accurate estimation of leak and other losses.

Typically, respiratory transitions are detected based on the measurements or estimates described above and react according to the magnitude and direction of the patient flow of the pressurized gas measurement. It is widely accepted that when flow and pressure are measured proximal to the patient in the absence of leak, such as typical in invasive applications, the detection of respiratory state is straightforward. However, this method, apart from being costly and bulky, fails when leak is present (e.g., when a tracheostomy cuff deflates). When measurements are done near the respiratory device, complex estimation algorithms are necessary to compensate for losses and leak. These methods fail when these losses are unpredictable or deviate from the assumptions and models used for fluid parameter estimation, e.g., when a caregiver administers a breathing treatment such as a nebulized flow of gas within the patient circuit or said caregiver adds or removes lossy components from a standard assumed patient circuit.

SUMMARY OF THE INVENTION

One aspect of the invention relates to a system and/or method for the identification of transitions in respiratory state without relying on measurement or estimation of flow at or near the airway of subject. Transitions in respiratory state may be identified based on changes in the first time derivative of flow at or near the airway of the subject. In some embodiments, an effort parameter is determined that approximates the second time derivative of flow. Based on comparisons of the effort parameter to a threshold, transitions in respiratory state are identified. The threshold may be dynamic to reduce false identifications of transitions in respiratory state.

Another aspect of the invention relates to a system configured to deliver a pressurized flow of breathable gas to the airway of a subject in accordance with a therapy regimen. In one embodiment, the system comprises a pressure generator, a sensor, and one or more processors. The pressure generator is configured to generate a pressurized flow of breathable gas for delivery to the airway of a subject. The sensor is configured to generate an output signal indicating flow of the pressurized flow of breathable gas. The one or more processors are configured to identify transitions in respiratory state based on changes in the first time derivative of flow of the pressurized flow of breathable gas, and to control the pressure generator to adjust a fluid parameter of the pressurized flow of breathable gas in accordance with a therapy regimen. The therapy regimen dictates that the fluid parameter varies as a function of respiratory state.

Yet another aspect of the invention relates to a method of delivering a pressurized flow of breathable gas to the airway of a subject in accordance with a therapy regimen. In one embodiment, the method comprises generating a pressurized flow of breathable gas for delivery to the airway of the subject; generating an output signal indicating flow of the pressurized flow of breathable gas; identifying transitions in respiratory state based on changes in the first time derivative of flow of the pressurized flow of breathable gas as indicated by the output signal; and adjusting a fluid parameter of the pressurized flow of breathable gas in accordance with a therapy regimen, wherein the therapy regimen dictates that the fluid parameter varies as a function of respiratory state.

A further aspect of the invention relates to a system configured to deliver a pressurized flow of breathable gas to the airway of a subject in accordance with a therapy regimen. In one embodiment, the system comprises means for generating a pressurized flow of breathable gas for delivery to the airway of the subject; means for generating an output signal indicating flow of the pressurized flow of breathable gas; means for identifying transitions in respiratory state based on changes in the first time derivative of flow of the pressurized flow of breathable gas as indicated by the output signal; and means for adjusting a fluid parameter of the pressurized flow of breathable gas in accordance with a therapy regimen, wherein the therapy regimen dictates that the fluid parameter varies as a function of respiratory state.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
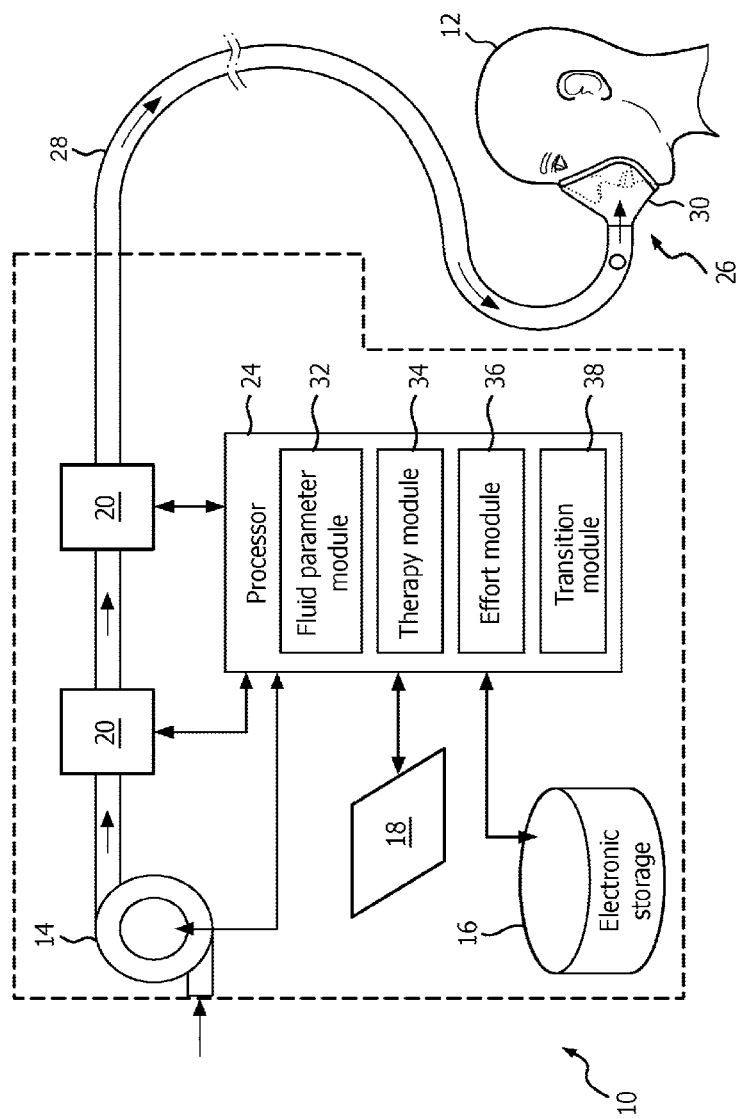
FIG. 1 illustrates a system configured to deliver a pressurized flow of breathable gas to the airway of a subject, in accordance with one or more embodiments of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to deliver a pressurized flow of breathable gas to the airway of a subject 12 in accordance with a therapy regimen. One or more fluid parameters of the pressurized flow of breathable gas are adjusted based on the respiratory state of subject 12. System 10 provides for identification of breathing transitions without relying on measurement or estimation of flow at or near the airway of subject 12. In one embodiment, system 10 includes one or more of a pressure generator 14, electronic storage 16, a user interface 18, one or more sensors 20, a processor 24, and/or other components. Processor 24 is configured to process data generated by sensors 20, determine the respiratory state of subject 12, and control pressure generator 14 in accordance with a therapy regimen that varies one or more parameters of the pressurized flow of breathable gas based on the respiratory state of the subject.

In one embodiment, pressure generator 14 is configured to generate a pressurized flow of breathable gas for delivery to the airway of subject 12. The pressure generator may control one or more parameters of the pressurized flow of breathable gas (e.g., flow, pressure, volume, humidity, temperature, gas composition, etc.) for therapeutic purposes, or for other purposes. The one or more parameters may be controlled in accordance with a therapy regimen (e.g., as discussed further below). The therapy regimen may be configured to sustain and/or otherwise improve the quality of life in subject 12. By way of non-limiting example, pressure generator 14 may be configured to control the pressure of the pressurized flow of breathable gas in order to treat respiratory insufficiency or obstructed airway syndrome. Pressure generator 14 may include a positive pressure generator configured to provide a positive airway pressure therapy to subject 12. Such a device is described, for example, in U.S. Pat. No. 6,105,575, the contents of which are hereby incorporated by reference in its entirety.

The pressurized flow of breathable gas is delivered to the airway of subject 12 via a subject interface 26. Subject interface 26 is configured to communicate the pressurized flow of breathable gas generated by pressure generator 14 to the airway of subject 12. As such, subject interface 26 includes a conduit 28 and an interface appliance 30. Conduit conveys the pressurized flow of breathable gas to interface appliance 30, and interface appliance 30 delivers the pressurized flow of breathable gas to the airway of subject 12. Some examples of interface appliance 30 may include, for example, an endotracheal tube, a nasal cannula, a nasal mask, a nasal/oral mask, a full face mask, a total face mask, or other interface appliances that communication a flow of gas with an airway of a subject. The present invention is not limited to these examples, and contemplates delivery of the pressurized flow of breathable gas to subject 12 using any subject interface.

Although FIG. 1 illustrates the configuration of system 10 with subject interface 26 as being a single-limb, passive system, this is not intended to be limiting. It will be appreciated that the scope of this disclosure includes embodiments in which the subject interface 26 is formed as a two-limbed system including a second conduit configured to receive exhalation from interface appliance 30. The second conduit may exhaust such fluid to atmosphere, may convey such fluid to a filter, and/or convey such fluid to other components including a component within system 10.

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 24, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., generator 14, user interface 18, processor 24, etc.).

User interface 18 is configured to provide an interface between system 10 and one or more users (e.g., subject 12, a caregiver, a researcher, a therapy decision-maker, etc.) through which the users may provide information to and receive information from system 10. This enables data, cues, results, and/or instructions and any other communicable items, collectively referred to as "information," to be communicated between the users and one or more of pressure generator 14, electronic storage 16, and/or processor 24. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with generator 14. User interface 18 may be configured to receive input from subject 12 to modify tunable parameters of system 10. For example, user interface 18 may be configured to receive input from subject 12 to modify or select sensitivity or response time of the respiratory state detection (e.g., the threshold level for breathing state transition detection may be adjusted for either an increase or a decrease in sensitivity with a graduated knob or a digital interface displaying a number from 1 to 10).

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

Sensors 20 are configured to generate one or more output signals conveying information related to one or more fluid parameters of the pressurized flow of breathable gas. The one or more parameters may include, for example, one or more of a flow, a volume, a pressure, a composition (e.g., concentration(s) of one or more constituents), humidity, temperature, acceleration, velocity, acoustics, changes in a parameter indicative of respiration, and/or other fluid parameters. In one embodiment sensors 20 are a flow sensor and a pressure sensor. The sensors may include one or more sensors that measure such parameters directly (e.g., through fluid communication with the pressurized flow of breathable gas at pressure generator 14 or in subject interface 26). The sensors may include one or more sensors that generate output signals related to one or more parameters of the pressurized flow of breathable gas indirectly. For example, one or more of sensors 20 may generate an output based on an operating parameter of pressure generator 14 (e.g., a valve driver or motor current, voltage, rotational velocity, and/or other operating parameters), and/or other sensors. Although sensors 20 are illustrated as two separate sensors disposed adjacent to pressure generator 14, this is not intended to be limiting. Sensors 20 may include one or more sensors disposed in single location or a plurality of locations, such as for example, within pressure generator 14, within (or in communication with) conduit 28, within (or in communication with) interface appliance 30, and/or other locations.

In some implementations, one or more of sensors 20 may be placed outside of system 10 and nearer to subject 12. In such implementations, the output signals generated by the externally located sensors 20 can be relayed to processor 24 by wired and/or wireless configuration. An independent user interface may be included with the externally located sensors 20 that receives the output signals generated by sensors 20, processes the output signals implementing some or all of the techniques described herein, and/or displaying at least some of the determined information.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device (e.g., pressure generator 14), or processor 24 may represent processing functionality of a plurality of devices operating in coordination.

Generally, processor 24 is configured to determine the respiratory state of subject 12. Processor 24 is further configured to control pressure generator 14 in generation of the pressurized flow of breathable gas such that one or more parameters of the pressurized flow of breathable gas vary in accordance with a therapy regimen that defines the one or more parameters as a function of respiratory state. To detect respiratory state, processor 24 may be configured to identify transitions in respiratory state based on the shape of flow (and/or other fluid parameters) of the pressurized flow of breathable gas. The identification of transitions in respiratory state may be independent from sensing and/or estimating fluid parameters at or near the airway of subject 12 (e.g., at interface appliance 30). As such, it may not require accurate leak and/or loss estimation. In some implementations, processor 24 may be configured to identify transitions in respiratory state based on changes in the first time derivative of flow.

As is shown in FIG. 1, processor 24 may be configured to execute one or more computer program modules. The one or more computer program modules may include one or more of a fluid parameter module 32, a therapy module 34, an effort module 36, a transition module 38, and/or other modules. Processor 24 may be configured to execute modules 32, 34, 36, and/or 38 by software; hardware; firmware; some combination of software, hardware, and/or firmware; and/or other mechanisms for configuring processing capabilities on processor 24.

It should be appreciated that although modules 32, 34, 36, and 38 are illustrated in FIG. 1 as being co-located within a single processing unit, in implementations in which processor 24 includes multiple processing units, one or more of modules 32, 34, 36, and/or 38 may be located remotely from the other modules. The description of the functionality provided by the different modules 32, 34, 36, and/or 38 described below is for illustrative purposes, and is not intended to be limiting, as any of modules 32, 34, 36, and/or 38 may provide more or less functionality than is described. For example, one or more of modules 32, 34, 36, and/or 38 may be eliminated, and some or all of its functionality may be provided by other ones of modules 32, 34, 36, and/or 38. As another example, processor 24 may be configured to execute one or more additional modules that may perform some or all of the functionality attributed below to one of modules 32, 34, 36, and/or 38.

The fluid parameter module 32 is configured to determine one or more fluid parameters of the pressurized flow of breathable gas. The fluid parameter module 32 determines the one or more fluid parameters of the pressurized flow of breathable gas based on the output signals generated by sensors 20. The one or more fluid parameters determined by breathing parameter module 32 may include a flow, a volume, a pressure, a composition (e.g., concentration(s) of one or more constituents), humidity, temperature, acceleration, velocity, acoustics, changes in a parameter indicative of respiration, and/or other fluid parameters.

The therapy module 34 is configured to control pressure generator 14 to adjust the parameters of the pressurized flow of breathable gas in accordance with a therapy regimen. The therapy regimen may dictate that breathing transitions by subject 12 should trigger corresponding changes in one or more fluid parameters of the pressurized flow of breathable gas. As used herein, the term "breathing parameters" may refer to transitions between inhalation and exhalation and/or transitions between exhalation and inhalation. The changes in the one or more fluid parameters of the pressurized flow of breathable gas corresponding to breathing transitions may include changes in flow (e.g., higher for inhalation, lower for exhalation), changes in pressure (e.g., higher for inhalation, lower for exhalation), and/or other changes in other parameters.

A non-limiting example of one such therapy regimen is bi-level positive air pressure therapy (BIPAP®). In bi-level positive air pressure therapy, two levels of positive air pressure (HI and LO) are supplied to a patient. Other modes of generating the pressurized flow of breathable gas are contemplated, such as C-Flex, Bi-Flex, PAV®, auto-titrating therapies, or combinations thereof. Generally, the timing of the HI and LO levels of pressure are controlled such that the HI level of positive air pressure is delivered to subject 12 during inhalation (known as Inspiratory Positive Airway Pressure or IPAP) and the LO level of pressure is delivered to subject 12 during exhalation (known as Expiratory Positive Airway Pressure or EPAP). The timing of adjustments to the parameters of the pressurized flow of breathable gas in accordance with a BiPAP® therapy regimen may be determined by therapy module 34. Another non-limiting example of a therapy regimen in which breathing transitions trigger changes to one or more fluid parameters is a ventilation therapy regimen in which the pressurized flow of breathable gas mechanically ventilates subject 12. The mechanical ventilation may assist respiratory effort provided by subject 12.

Effort module 36 is configured to determine a respiratory effort parameter. The effort parameter may reflect respiratory effort, and is used to identify breathing transitions. The effort parameter is calculated based on changes in the first time derivative of flow of the pressurized flow of breathable gas.

Effort module 36 is configured such that the effort parameter for a given point in time is determined as a function of a difference between the slope of flow (e.g., the first time derivative of flow) of the pressurized flow of breathable gas after the given point in time and the slope of flow of the pressurized flow of breathable gas before the given point in time. The slope of flow of the pressurized flow of breathable gas is determined from determinations of flow by fluid parameter module 32, which, in turn, are based on the output signals generated by sensors 20.

Figure 2:
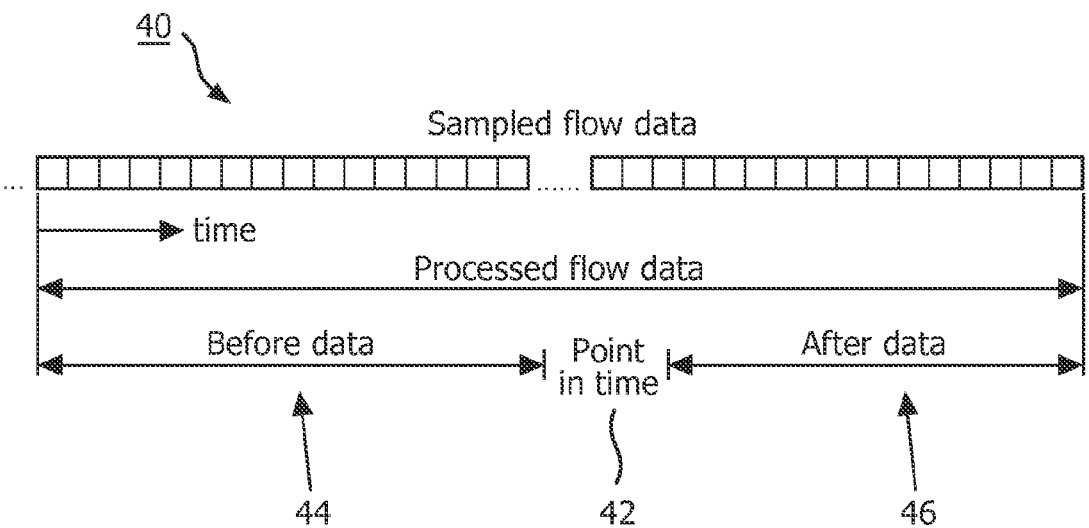
FIG. 2 illustrates a set of samples of flow, in accordance with one or more embodiments of the invention.

By way of illustration, FIG. 2 a sequence 40 of samples of the flow of the pressurized flow of breathable gas prior to a point in time 42 for which the effort parameter is being determined. It will be appreciated a "point in time" may refer to a single, discrete point in time, or a period of time spanning some relatively small amount of time. The samples of flow included in sequence 40 may represent information conveyed in the output signal of a sensor measuring flow (e.g., sensors 20 in FIG. 1) and/or determinations of flow made by a processor based on such an output signal (e.g., determinations of flow by fluid parameter module 32 in FIG. 1). Sequence 40 includes a first series of samples 44 and a second series of samples 46. The first series of samples 44 are samples of flow of the pressurized flow of breathable gas prior to point in time 42, and the second series of samples 46 are samples of flow of the pressurized flow of breathable gas subsequent to point in time 42. The effort parameter is determined based on a difference between the slope of the second series of samples 46 and the slope of the first series of samples 44.

The slope, or first time derivative, of flow of the pressurized flow of breathable gas is the rate of change of flow of the pressurized flow of breathable gas ($\Delta Q/t$).

It will be appreciated that respiration by the subject causes changes in flow of the pressurized flow of breathable gas corresponding to inhalation (e.g., increased flow by convention) during which gas is accepted into the airway of the subject and exhalation (e.g., decreased flow by convention) during which gas is expelled from the airway of the subject. Thus consistent with this convention, the effort parameter, which is determined at a given point in time as the difference between the slope of flow in the past and the slope of flow in the future, increases at the beginning of inhalation and at the peak of exhalation. Furthermore, the effort parameter decreases at the beginning of expiration and at the peak of inhalation.

The first series of samples 44 span a period of time prior to point in time 42. This period of time may be less than or equal to about 100 milliseconds, less than or equal to about 150 milliseconds, less than or equal to about 210 milliseconds, less than or equal to about 300 milliseconds, less than or equal to about 1 second, and/or some other period of time. The size of the first series of samples 44 is chosen such that the period of time spanned by the first period of samples 44 represents an average and stable period of flow. The second series of samples 46 may be selected to span a period of time substantially the same as the period of time corresponding to the first series of samples 44, or may be selected to span a shorter period of time. The length of the period of time corresponding to the second series of samples 46 may be chosen to be an appropriate response time for detecting transitions in respiratory state. For example, the size of the second set of samples 46 may be selected to correspond to a time period less than or equal to about 150 milliseconds, less than or equal to about 100 milliseconds, less than or equal to about 90 milliseconds, and/or other time periods. In one embodiment, the second set of samples 46 corresponds to a period of time of about 90 milliseconds. This period of time is small enough to be imperceptible and/or unobstrusive to the subject. However, this example should not be viewed as limiting.

Figure 3:
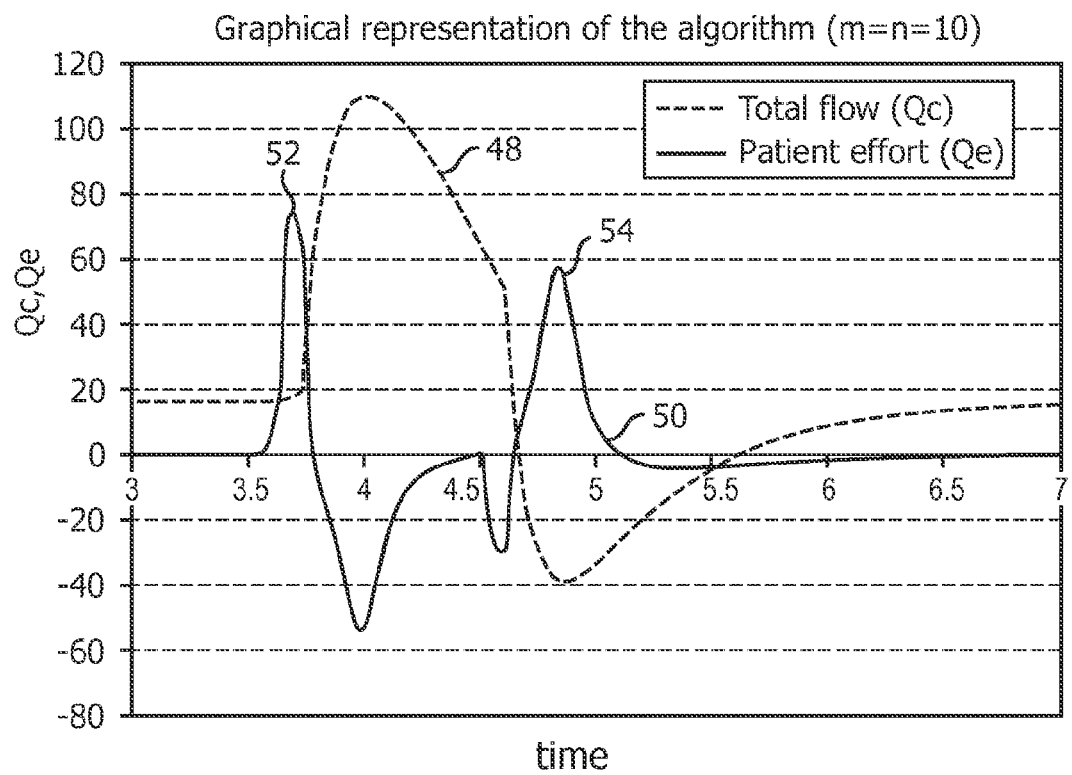
FIG. 3 illustrates a set of plots showing the relationship between an effort parameter and breathing transitions, according to one or more embodiments of the invention.

By way of illustration, FIG. 3 depicts a plot 48 of the flow of a pressurized flow of breathable gas being delivered to the airway of a subject, and a plot 50 of the effort parameter for the flow samples represented by plot 48. As can be seen in FIG. 3, a first spike 52 in plot 50 occurs at or near the beginning of inhalation as flow increases steeply, and a second spike 54 occurs at or near the peak of exhalation.

Returning to FIG. 1, in conventional systems, detection of breathing transitions is typically performed from direct analysis of the flow waveform and/or samples. In conventional analysis, reliance was placed on the analyzed waveform and/or samples being indicative of flow at or near the airway of subject 12 (e.g., at interface appliance 30). However, in order to obtain a waveform and/or samples that accurately indicated flow at or near the airway of subject 12, conventional systems would have either included a sensor disposed at interface appliance 30 (or directly adjacent thereto), or accurately estimate leak within subject interface 26. The cost associated with including a sensor at interface appliance 30 typically discouraged the use of such sensors, and conventional leak estimation techniques proved to be somewhat imprecise and/or inaccurate. By contrast, the determination of the effort parameter by effort module 36 is not overly sensitive to leak, and facilitates reliable detection of breathing parameters without the cost associated with a sensor located at or near the airway of subject 12 and without being reliant on leak estimation. This does not preclude from the scope of this disclosure embodiments in which system 10 implements leak estimation and/or a sensor disposed at or near the airway of subject 12.

In one embodiment, effort module 36 is configured to determine the slope of flow before a given point in time and the slope of flow after a given point in time using a linear least squares method. It will be appreciated that this is not intended to be limiting, as the slope of flow signals may be calculated using a variety of mathematical techniques without departing from the scope of this disclosure. Turning back to FIG. 2, the slope of first series of samples 44 and the slope of second series of samples 46 may be determined by a linear least squares method. The first series of samples 44 can be expressed as $Q_b(n)$, and the second series of samples 46 can be expressed as $Q_a(m) \cdot Q_b(n)$ and $Q_a(m)$ can be expressed in matrix form as:

$$Q_b = \begin{bmatrix} Q_{b1} \\ \vdots \\ \vdots \\ Q_{b_{n-1}} \\ Q_{b_n} \end{bmatrix} \text{ and } Q_a = \begin{bmatrix} Q_{a1} \\ \vdots \\ \vdots \\ Q_{a_{m-1}} \\ Q_{a_m} \end{bmatrix}, \quad \text{Eq. (1).}$$

The linear least squares method involves fitting these samples to the linear model:

$$Q_a = A_1 + A_2 \cdot t_a \text{ or } Q_a = At_a; \text{ and}$$

$$Q_b = \beta_1 + \beta_2 \cdot t_b \text{ or } Q_b = \beta t_b \quad \text{Eq. (2).}$$

where t is the equally spaced time matrix:

$$t_b = \begin{bmatrix} 1 & 1 \\ 1 & 2 \\ \vdots & \vdots \\ \vdots & \vdots \\ 1 & n \end{bmatrix} t_a = \begin{bmatrix} 1 & 1 \\ 1 & 2 \\ \vdots & \vdots \\ \vdots & \vdots \\ 1 & m \end{bmatrix}, \quad \text{Eq. (3).}$$

Using the least squares method:

$$(t_b^T t_b)\beta = t_b^T Q_b; \text{ and}$$

$$(t_a^T t_a)A = t_a^T Q_a \quad \text{Eq (4)}$$

Solving for β and A gives:

$$\beta = (t_b^T t_b)^{-1} t_b^T Q_b; \text{ and}$$

$$A = (t_a^T t_a)^{-1} t_a^T Q_a \quad \text{Eq. (5),}$$

The slopes, $m_a$ and $m_b$, of the first series of samples 44 and second series of samples 46 can be extracted from β and A by using the value in the second row. The effort parameter ($Q_e$) for point in time 42 is then computed as:

$$Q_e = (m_a - m_b) \cdot \text{Gain}, \quad \text{Eq (6)}$$

Determination of the effort parameter in accordance with the technique set forth above approximates the second time derivative of flow of the pressurized flow of breathable gas. It will be appreciated that any mathematical approximation of the second time derivative of flow is a reasonable variation of this technique, and would fall within the scope of this disclosure.

Referring back to FIG. 1, effort module 36 is configured such that the gain (Gain) used to determine the effort parameter is constant or dynamic. Dynamic determination of the gain may be based on one or more of flow, time, tidal volume, and/or other parameters. The determination of gain may be bifurcated (e.g., using one relationship to determine gain above a flow threshold and using a different relationship to determine gain below the flow threshold). For example, effort module 36 may be configured to determine gain according to the following relationships:

$$\text{Gain} = \begin{Vmatrix} \dfrac{(\text{Peak\_gain} - 2) \cdot nAvgFlow}{10 + 2} & \text{for nAvg\_Flow} \leq 10 \, lpm \\ \dfrac{(8 - \text{Peak\_gain}) \cdot (AvgFlow - 24)}{14 + 8} & \text{for nAvg\_Flow} > 10 \, lpm. \end{Vmatrix} \quad \text{Eq. (7).}$$

It will be appreciated that the setting of 10 liters per minute as the flow threshold is not intended to be limiting. Nor are the values of the constants provided in equation (7). Instead, these values are merely provided as non-limiting examples.

In one embodiment, the peak gain is a value that is determined based on a user-selectable setting (e.g., via user interface 18) for sensitivity and/or the tidal volume of subject 12. The tidal volume may be received via user-selection (e.g., via user interface 18), determined based on the output signals of sensors 20, and/or otherwise determined. In one embodiment, peak gain is determined in accordance with the following relationship:

$$\text{Peak\_Gain} = k - \text{Sensitivity} * 10 + \frac{nMaxVol}{Vti}, \quad \text{Eq. (8)}.$$

where the Sensitivity is a user-adjustable whole number; Vti represent the typical inhaled tidal volume of subject 12, nMaxVol represents the maximum expected tidal volume, and k represents an arbitrary constant either predetermined or selected through user interface 18. In one embodiment, k is chosen to be 65, nMaxVol is set as 2 liters.

Transition module 38 is configured to identify breathing transitions in the respiration of subject 12 based on the effort parameter. In one embodiment, transition module 38 is configured to compare determinations of the effort parameter by effort module 36 with a threshold level. Responsive to the effort parameter breaching the threshold level, transition module 38 is configured to identify a breathing transition, which, in turn, triggers therapy module 34 to adjust one or more fluid parameters of the pressurized flow of breathable gas in accordance with the therapy regimen.

Transition module 38 is configured such that the threshold level is determined based on one or more of a predetermined level, a user-selectable setting, an estimation of noise, as a function of time since the previous identified breathing transition, a measurement of a fluid parameter of the pressurized flow of breathable gas, and/or other parameters. The predetermined level may be a level determined at the time of manufacture, at a software or firmware update, through calibration, and/or at other times. Selection of the user-selectable setting may be received via user interface 18. The user-selectable setting may be implemented to adjust the predetermined level. For example, a user-selectable sensitivity setting of 1 may result in the threshold level for the effort parameter being set at the predetermined level plus 1, while a user-selectable sensitivity setting of 2 may result in the threshold level for the effort parameter being set at the predetermined level plus 2, and so on.

In one embodiment, transition module 38 is configured such that the threshold level of the effort parameter is increased to account for an estimated level of noise in the determinations of the effort parameter. To distinguish the effort of subject 12 from noise, the amount by which the threshold level is increased may include a fraction (e.g., about ¼) of the peak to peak value of recent determinations of the effort parameter by effort module 36, a fraction (e.g., about ⅓) of the maximum continuous fall of the effort parameter, and/or other values. In one embodiment, the amount by which the threshold level is increased is the greater of ¼ of the peak to peak value of the effort parameter in the previous 600 milliseconds or ⅓ of the maximum continuous fall of the effort parameter in that same time period.

In one embodiment, transition module 38 is configured to add an amount to the threshold level of the effort parameter that decays with time away from the previous identification of a breathing transition. The amount may decay to zero. This may reduce incidents in which one breathing transition is falsely identified just after a preceding breathing transition has been identified. The decay may be linear or exponential. The rate of decay may be determined based on an expected respiratory cycle of subject 12, a user-selectable setting, and/or other parameters.

During operation of system 10, changes in flow of pressurized flow of breathable gas typically come from one of two sources: respiration by subject 12 and operation of pressure generator 14. Changes in flow caused by operation of pressure generator 14 may cause increases in the determination of the effort parameter that are not associated with respiration by subject 12. Generally, an increase in flow caused by pressure generator 14 will be accompanied by an increase in pressure. As such, transition module 38 may be configured to vary the threshold amount as a function of pressure of the pressurized flow of breathable gas. The pressure may be obtained by transition module 38 from the output signals of sensors 20 and/or from determinations by fluid parameter module 32. In one embodiment, transition module 38 varies the threshold level of the effort parameter as a function of the slope of pressure.

Figure 4:
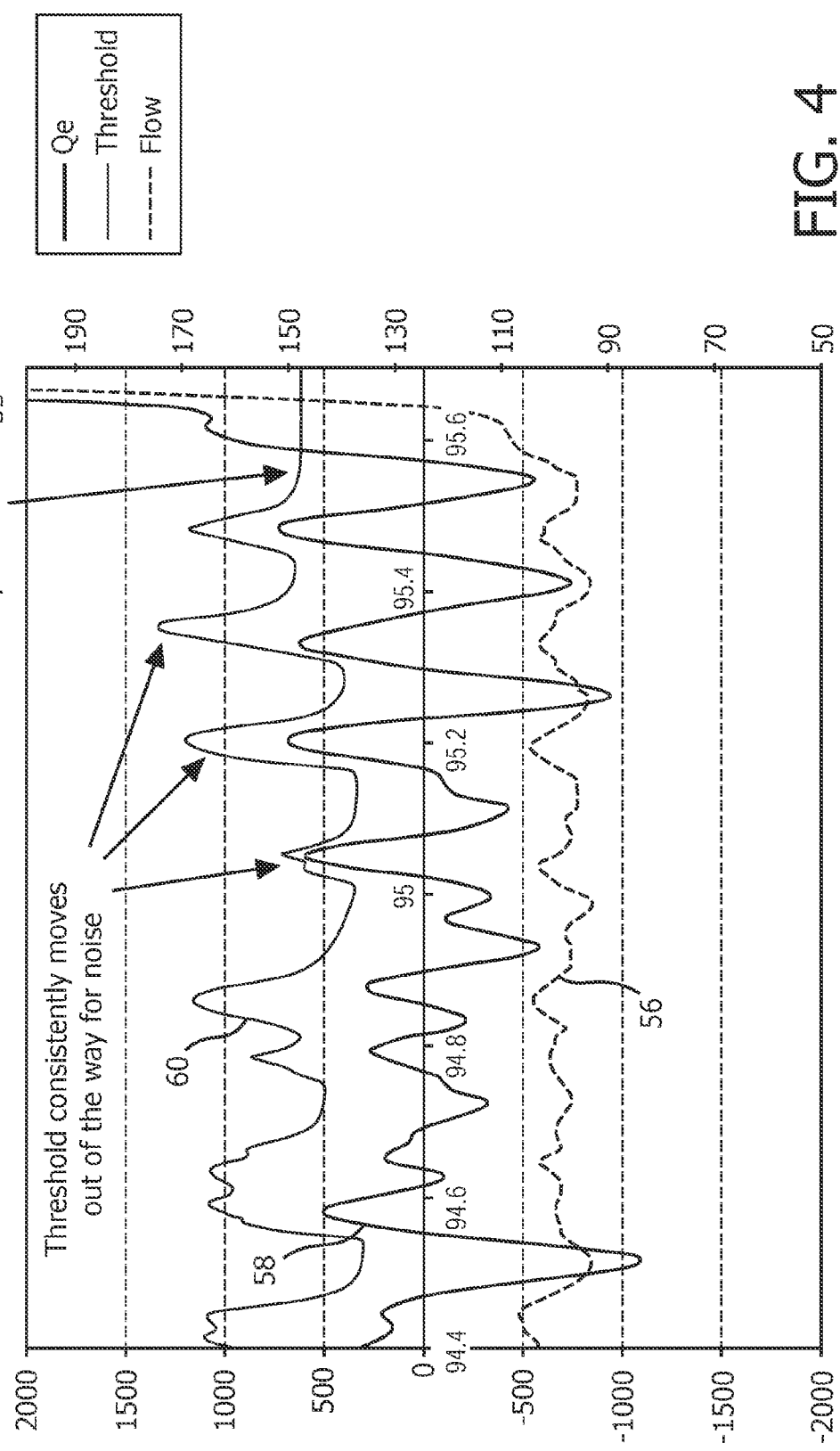
FIG. 4 illustrates a set of plots showing how a dynamic threshold level reduces false detections of breathing transitions, in accordance with one or more embodiments of the invention.

In one embodiment, transition module 38 varies the threshold level of the effort parameter as a function of a difference between more recent pressure (e.g., about 70 milliseconds old) and a less recent pressure (e.g., about 200 milliseconds old). The less recent pressure may be filtered with a low-pass filter prior to determination of the difference. By way of illustration, FIG. 4 depicts a plot 56 of flow, a plot 58 of the effort parameter, and a plot 60 of a threshold level of the effort parameter adjusted based on the change in pressure (e.g., as described above). As can be seen in FIG. 4, this adjustment to the threshold level moves the threshold level out of the way of noise caused by operation of a pressure generator while keeping the threshold level low for effort parameter increases caused by the subject. This methodology allows for more accurate identifications of transitions in respiratory states of the subject.

Returning to FIG. 1, in one embodiment transition module 38 identifies breathing transitions based on a number of temporally close determinations of the effort parameter breaching the threshold level. The transition module 38 may require the determinations to be consecutive, or transition module 38 may require the determinations to be made within some period of time. The number may be 1 or more than 1. The number may be determined based on a permanent (or semi-permanent) setting, based on a user-selectable setting, and/or other parameters.

In one embodiment, transition module 38 is configured to reduce incidents of a phenomenon called "back-end triggering". Back-end triggering occurs when a breathing transition from exhalation to inhalation is missed, and the increase in the effort parameter at the peak of exhalation is mistakenly identified as the start of inhalation. This may result in pressure being increased as subject 12 attempts to exhale or some form of inappropriate therapy according to the therapy regimen. By way of illustration, in FIG. 3, if first spike 52 is not identified as initiation of inhalation, second spike 54 may be identified as the initiation of inhalation. This would result in inappropriate therapy following second spike 54.

Returning back to FIG. 1, in order to reduce incidents of back-end triggering, transition module 38 may be configured such that responsive to the slope of flow becoming negative (e.g., a slope of flow determined by effort module 36 to determine the effort parameter) and/or the flow itself becoming negative, the trigger is revoked. The revocation may remain in place for some predetermined period of time. While the trigger is revoked, instances of the effort parameter breaching the threshold level (e.g., at the peak of the next exhalation) do not result in identification of a breathing transition. Thus, the fluid parameters of the pressurized flow of breathable gas will remain at the expiration level (e.g., EPAP) until the trigger is revoked and a spike in the effort parameter is detected indicating the next inspiration has begun.

Figure 5:
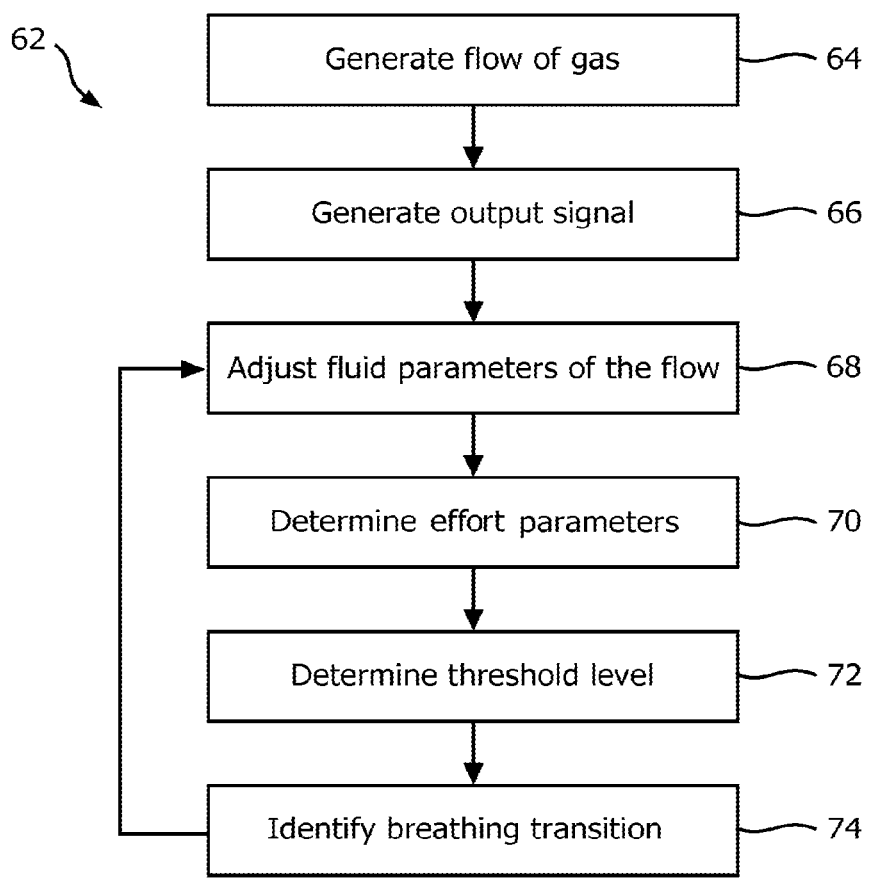
FIG. 5 illustrates a method of identifying breathing transitions in the respiration of a subject, according to one or more embodiments of the invention.

FIG. 5 illustrates a method 62 of identifying breathing transitions in the respiration of a subject. The operations of method 62 presented below are intended to be illustrative. In some embodiments, method 62 may be accomplished with one or more additional operations not described, and/or without one or more of the operations discussed. Additionally, the order in which the operations of method 62 are illustrated in FIG. 5 and described below is not intended to be limiting.

In some embodiments, method 62 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 62 in response to instructions stored electronically on an electronic storage medium. The one or more processing devices may include one or more devices configured through hardware, firmware, and/or software to be specifically designed for execution of one or more of the operations of method 62.

At an operation 64 a pressurized flow of breathable gas is generated for delivery to the airway of the subject. In one embodiment, operation 64 is performed by a pressure generator similar to or the same as pressure generator 14 (shown in FIG. 1 and described above).

At an operation 66, one or more output signals are generated conveying information related to one or more fluid parameters of the pressurized flow of breathable gas. In one embodiment, operation 66 is performed by one or more sensors similar to or the same as sensors 20 (shown in FIG. 1 and described above).

At an operation 68, one or more fluid parameters of the pressurized flow of breathable gas are adjusted in accordance with a therapy regimen. The therapy regimen dictates that breathing transitions by the subject should trigger corresponding changes in the one or more fluid parameters of the pressurized flow of breathable gas. In one embodiment, operation 68 is performed by a pressure generator similar to or the same as pressure generator 14 under the control of a therapy module similar to or the same as therapy module 34 (shown in FIG. 1 and described above).

At an operation 70, an effort parameter is determined of the respiration of the subject is determined. The effort parameter is determined based on the output signals generated at operation 66. The effort parameter at a given point in time is determined as function of a difference between a slope of flow subsequent to the given point in time and a slope of flow prior to the given point in time. In one embodiment, operation 70 is performed by an effort module similar to or the same as effort module 36 (shown in FIG. 1 and described above).

At an operation 72, a threshold level of the effort parameter is determined. The threshold level may be determined based on one or more of a predetermined level, a user-selectable setting, an estimation of noise, as a function of time since the previous identified breathing transition, a measurement of a fluid parameter of the pressurized flow of breathable gas, and/or other parameters. In one embodiment, operation 72 is performed by a transition module similar to or the same as transition module 38.

At an operation 74, a breathing transition in the respiration of the subject is identified. The breathing transition is identified based on the effort parameter. The effort parameter is compared with the threshold level. Breach of the threshold level by the effort parameter results in identification of a breathing transition. In one embodiment, operation 74 is performed by a transition module similar to or the same as transition module 38 (shown in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to deliver a pressurized flow of breathable gas to an airway of a subject in accordance with a therapy regimen, the system comprising:
    a pressure generator configured to generate a pressurized flow for delivery to the airway of the subject, wherein the pressurized flow includes breathable gas;
    a pressure sensor, proximate the pressure generator and remote from the subject, configured to measure pressure generated by the pressure generator;
    a sensor configured to generate output signals indicating flow of the pressurized flow; and
    one or more hardware processors configured by machine-readable instructions to:
        determine a fluid parameter of the pressurized flow based on the output signals;
        determine an effort parameter such that the effort parameter for a given point in time is determined as a function of the difference between a first slope of the fluid parameter after the given point in time and a second slope of the fluid parameter before the given point in time; and
        identify transitions in respiratory state based on comparisons of the effort parameter with a threshold effort parameter level, and control the pressure generator to adjust the pressurized flow of breathable gas in accordance with a therapy regimen, wherein the therapy regimen dictates that one or more fluid parameter levels of the pressurized flow of breathable gas vary based on the identified transitions in respiratory state; and
        adjust the threshold effort parameter level based on the measured pressure from the pressure sensor.

2. The system of claim 1, wherein the one or more hardware processors are further configured to increase the threshold effort parameter level based on an estimated level of noise in determinations of the effort parameter.

3. The system of claim 2, wherein the one or more hardware processors are further configured to base an amount by which the threshold effort parameter level is increased on peak to peak values of recent determinations of the effort parameter.

4. The system of claim 1, wherein the one or more hardware processors are further configured to adjust the threshold effort parameter level by an amount that decays with time over multiple respiratory cycles.

5. The system of claim 1, wherein the threshold effort parameter level is adjusted based on a slope of the measured pressure from the pressure sensor.

6. A method of identifying transitions in respiratory state of a subject with an identification system, the identification system comprising a pressure generator, a sensor, and one or more hardware processors, the method comprising:

generating, with the pressure generator, a pressurized flow for delivery to the airway of the subject, wherein the pressurized flow includes breathable gas;

generating, with the sensor, an output signal indicating flow of the pressurized flow of breathable gas;

measuring a pressure generated by the pressure generator;

determining, with the one or more hardware processors, based on the output signal, an effort parameter such that the effort parameter for a given point in time is determined as a function of the difference between a first slope of the pressurized flow after the given point in time and a second slope of the pressurized flow before the given point in time;

identifying, with the one or more hardware processors, transitions in respiratory state based on comparisons of the effort parameter with a threshold effort parameter level; and adjusting, with the one or more hardware processors, a fluid parameter of the pressurized flow of breathable gas in accordance with a therapy regimen, wherein the therapy regimen dictates that the fluid parameter varies based on the identified transitions in respiratory state and adjusting the threshold effort parameter level based on the measured pressure generated by the pressure generator.

7. The method of claim 6, wherein the threshold effort parameter level is increased, by the one or more hardware processors, based on an estimated level of noise in determinations of the effort parameter.

8. The method of claim 7, wherein an amount by which the threshold effort parameter level is increased by the one or more hardware processors is based on peak to peak values of recent determinations of the effort parameter.

9. The method of claim 6, further comprising:
adjusting, with the one or more hardware processors, the threshold effort parameter level by an amount that decays with time over multiple respiratory cycles.

10. A system configured to deliver a pressurized flow of breathable gas to the airway of a subject in accordance with a therapy regimen, the system comprising:
means for generating a pressurized flow for delivery to the airway of the subject, wherein the pressurized flow includes breathable gas;
means for measuring a pressure generated by the pressure generator;
means for generating output signals indicating flow of the pressurized flow of breathable gas;
means for determining a fluid parameter of the pressurized flow based on the output signals;
means for determining an effort parameter such that the effort parameter for a given point in time is determined as a function of the difference between a first slope of the fluid parameter after the given point in time and a second slope of the fluid parameter before the given point in time;
means for identifying transitions in respiratory state based on comparisons of the effort parameter with a threshold effort parameter level and adjusting the threshold effort parameter level based on the measured pressure generated by the pressure generator; and
means for adjusting the pressurized flow of breathable gas in accordance with a therapy regimen, wherein the therapy regimen dictates that one or more fluid parameter levels vary based on the identified transitions in respiratory state.

11. The system of claim 10, wherein the means for identifying transitions is further configured to increase the threshold effort parameter level based on an estimated level of noise in determinations of the effort parameter.

12. The system of claim 11, wherein the means for identifying transitions is further configured to base an amount by which the threshold effort parameter level is increased on peak to peak values of recent determinations of the effort parameter.

13. The system of claim 10, wherein the means for identifying transitions is further configured to adjust the threshold effort parameter level by an amount that decays with time over multiple respiratory cycles.

14. The system of claim 10, wherein the means for identifying transitions is further configured to adjust the threshold effort parameter level based on a slope of the measured level of pressure of the pressurized flow.

15. The system of claim 1, wherein the one or more hardware processors are further configured to determine the effort parameter such that the effort parameter increases to a first peak level at or near a beginning of inhalation and increases to a second peak level at or near a peak of exhalation.

16. The method of claim 6, wherein the determined effort parameter increases to a first peak level at or near a beginning of inhalation and increases to a second peak level at or near a peak of exhalation.

17. The system of claim 10, wherein the means for determining the effort parameter are further configured to determine the effort parameter such that the effort parameter increases to a first peak level at or near a beginning of inhalation and increases to a second peak level at or near a peak of exhalation.

18. The system of claim 1, wherein the one or more hardware processors are further configured to reduce back-end triggering, back-end triggering comprising a failure to identify a breathing transition from exhalation to inhalation such that an increase in the effort parameter at a peak of exhalation is mistakenly identified as a start of inhalation, and wherein reducing back-end triggering comprises, responsive to determining that a slope of the fluid parameter is negative and/or a flow of breathable gas is negative, the one or more hardware processors controlling the pressure generator such that the fluid parameter of the pressurized flow of breathable gas remains at an expiration level, wherein the expiration level indicates expiratory positive airway pressure, generated by the pressure generator, delivered to the subject during exhalation.

19. The method of claim 6, further comprising reducing back-end triggering, back-end triggering comprising a failure to identify a breathing transition from exhalation to inhalation such that an increase in the effort parameter at a peak of exhalation is mistakenly identified as a start of inhalation, and wherein reducing back-end triggering comprises, responsive to determining that a slope of the fluid parameter is negative and/or a flow of breathable gas is negative, controlling the pressure generator, with the one or more hardware processors, such that the fluid parameter of the pressurized flow of breathable gas remains at an expiration level, wherein the expiration level indicates expiratory positive airway pressure, generated by the pressure generator, delivered to the subject during exhalation.

20. The system of claim 10, wherein the means for adjusting the pressurized flow of breathable gas is configured to reduce back-end triggering, back-end triggering comprising a failure to identify a breathing transition from exhalation to inhalation such that an increase in effort parameter at a peak of exhalation is mistakenly identified as a start of inhalation, and wherein reducing back-end triggering comprises, responsive to determining that a slope of the fluid parameter is negative and/or a flow of breathable gas is negative, the means for adjusting the pressurized flow of breathable gas controlling the means for generating a pressurized flow such that the fluid parameter of the pressurized flow of breathable gas remains at an expiration level, wherein the expiration level indicates expiratory positive airway pressure, generated by the pressure generator, delivered to the subject during exhalation.

* * * * *